(12) United States Patent
Hansen et al.

(10) Patent No.: US 8,669,065 B1
(45) Date of Patent: Mar. 11, 2014

(54) METHODS FOR IDENTIFYING MOLECULES THAT MODULATE LIPID BINDING SITES OF ION CHANNELS

(76) Inventors: Scott B Hansen, Jupiter, FL (US); Andrew S Hansen, Bountiful, UT (US)

( * ) Notice: Subject to any disclaimer, the term of this patent is extended or adjusted under 35 U.S.C. 154(b) by 0 days.

(21) Appl. No.: 13/597,253

(22) Filed: Aug. 28, 2012

Related U.S. Application Data

(60) Provisional application No. 61/528,278, filed on Aug. 28, 2011.

(51) Int. Cl.
*G01N 33/53* (2006.01)
*G01N 33/567* (2006.01)

(52) U.S. Cl.
USPC ........................................ 435/7.2

(58) Field of Classification Search
None
See application file for complete search history.

(56) References Cited

U.S. PATENT DOCUMENTS 8,263,754 B2 * 9/2012 Gellman et al. ............. 536/17.9
2012/0190048 A1 * 7/2012 Trinquet et al. ............. 435/7.21

OTHER PUBLICATIONS

Lensink MF, et al. J. Biol. Chem. 285(14):10519-10526, Apr. 2, 2010 (available online at—DOI 10.1074/jbc.M109.068890).*
Yin H, et al. J. Biol. Chem, 284(18):12328-12338, May 1, 2009 (available online at—DOI 10.1074/jbc.M806516200).*
Im D-S. J. Lipid Res. 45:410-418, 2004.*
Kalipatnapu S, et al. Life 57(7):505-512, Jul. 2005.*

* cited by examiner

*Primary Examiner* — Robert Landsman
(74) *Attorney, Agent, or Firm* — Workman Nydegger

(57) ABSTRACT

A method for identifying molecules that selectively bind to a lipid binding site of a native integral membrane bound protein, includes (i) providing a solubilized integral membrane protein in a detergent micelle and having a native folding conformation; (ii) providing a soluble lipid analog that binds to the integral membrane protein at the native lipid binding site and causes a change in fluorescence of a fluorophore when bound as compared to unbound; and (iii) screening the solubilized integral membrane protein for binding to a plurality of compounds.

19 Claims, No Drawings

METHODS FOR IDENTIFYING MOLECULES THAT MODULATE LIPID BINDING SITES OF ION CHANNELS

BACKGROUND

Integral membrane proteins (i.e., membrane proteins permanently associated with a cell membrane) are currently being studied for their potential as drug targets. Many membrane proteins such as ion channels and G-protein coupled receptors are involved in the function and/or regulation of excitable cells. It is well known that integral membrane proteins are potential valuable drug targets for treating human disease and disorders. Current methods of screening integral membrane proteins for binding to ligands is generally carried out in whole cells. This technique has the advantage of using the proteins in their native environment which ensures proper function of the protein. Moreover, the compounds that are screened are generally small molecules and/or peptides. While techniques for screening membranes proteins have advanced dramatically in the recent years, these techniques have failed to produce clear results in a high throughput format. There continues to be a long felt but unmet need for methods that can identify novel compounds and novel mechanisms for modulating integral membrane proteins.

DETAILED DESCRIPTION

I. Introduction

The present disclosure relates to methods for screening integral membrane proteins for lipids that bind with specificity to lipid binding sites on the integral membrane protein. The present disclosure also relates to soluble lipid analogs that bind to the lipid binding site of the soluble lipid and cause a change in fluorescence in response to specific binding to a solubilized integral membrane protein.

The lipid analogs are soluble forms of insoluble lipids that bind to membrane proteins in cells. The soluble lipid analogs (also referred to herein as soluble lipid probes) mimic insoluble lipids that modulate integral membrane proteins. However, because the probes are soluble, they bind to solubilized membrane proteins rather than insert themselves into the native membrane environment. The soluble lipid probes include a fluorescence activating moiety that causes a change in fluorescence in a sample when the probe binds with specificity to the membrane protein. The fluorescence activating moiety can be a fluorescent fusion protein or a radio label that causes fluorescence of a scintillate.

The method disclosed herein relate to providing a soluble lipid probe in an aqueous solution, (providing a solubilized integral membrane protein having a native conformation.

The term "native conformation" of a membrane protein shall mean the protein has a tertiary structure that is sufficiently similar to the protein's native tertiary structure in the cell membrane so as to bind its native lipid ligand with specificity. In contrast, for example, proteins that have been denatured in harsh ionic detergents such as sodium dodecyl sulfide do not have a "native conformation."

The present disclosure relates to methods and systems for screening the integral membrane proteins for specific ligand binding of molecules that are not known to bind with specificity or high affinity to lipid binding sites of integral membrane proteins. The methods of the invention use properly folded solubilized integral membrane proteins (i.e., natively folded proteins) in detergent micelles to screen for specific binding by intracellular molecules. In some embodiment, the methods use fluorescently tagged and/or radiolabelled endogenous intracellular molecules to screen membrane proteins for novel binding sites on the intracellular domain. Binding of the intracellular molecules to the intracellular domain of the membrane protein can cause a change in a fluorescence emission (either increase or decrease) as compared to the emission when the intracellular molecules are not bound. The change in fluorescence is indicative of selective binding to the intracellular domain.

There are thousands of integral membrane proteins for which the gene sequence is known and the importance of the protein in the body is not understood. Many of these proteins are grouped into classes based on sequence homology. For example, a protein sequence may show homology to a membrane protein such as a particular type of transporter protein (e.g., ion channel), seven-transmembrane domain receptor, voltage gated channel or mechano-sensitive protein. From the protein sequence it may be apparent that the protein binds a particular known ligand such as GABA, acetylcholine, serotonin, glycine, an opioid, etc. Alternatively it may be apparent that the membrane protein belongs to a class of proteins sensitive to voltage or mechanical changes. The general function of these proteins (i.e., their response to a particular ligand, change in voltage, or mechanical change) can usually be correctly assumed to be the same as the homologous proteins. For example a protein that has a sequence that is homologous to an acetylcholine receptor can usually be correctly assumed to form an ion channel that is gated by acetylcholine. While sequence homology can be used to identify the general mechanisms of protein function (and thus the ligands that directly control that mechanism), sequence homology and protein classification cannot provide information regarding how differences in homologous membrane proteins (e.g., subtypes) relate to differences in biological function.

A current problem in drug discovery is a lack of specificity of drugs for particular protein subtypes. This lack of specificity may be the result of drug screens that tend to target the ligand binding that is common between different subtypes. For example, drug screens for acetylcholine receptors generally target binding sites that are common to all acetylcholine receptors and the molecules being screened mimic known ligands to that site. For example, when the target site is the acetylcholine binding site, the drug targets are selected that mimic the structure of acetylcholine or other molecules that bind to the acetylcholine binding site.

It is also known that lipids are important to regulation of many of these integral membrane proteins. Surprisingly and unexpectedly, Applicant's data confirms that integral membrane proteins bind lipids with specificity (i.e., in a similar way that small molecule agonist bind to receptor activation sites). The present invention relates to identifying molecules that bind to the lipid binding sites, identifying new lipid binding and fluorescent probes that can be used to screen for novel molecules that bind to the lipid binding sites.

The methods identify binding sites for endogenous molecules that are distinct from the critical binding site known to provide protein function (e.g., gating in a channel protein) for a particular class of membrane proteins (e.g., nicotinic receptors). Endogenous molecules found to bind with high affinity to the lipid binding sites of integral membrane proteins are useful for developing drug screening assays.

Moreover, because these binding sites are distinct from the main activation sites the binding sites are useful for developing allosteric modulators with selectivity between protein subtypes.

The methods described herein are particularly advantageous for screening cell membrane receptors (e.g., neuroreceptor) or proteins that have multiple transmembrane domains such as, but not limited to transporter proteins (e.g., ion channels) and seven-transmembrane domain receptors. These proteins have ligand binding sites that are generally known (e.g., the gating ligand in channel proteins) and the known ligand binding site is generally extracellular. Transmembrane proteins with an extracellular domain that binds a known ligand often have an intracellular domain with unknown function. This domain is usually removed when preparing the protein for crystallography because it is usually disordered and disordered proteins do not crystallize well. The lack of crystal structures and the difficulty of screening the inside of a cell has led to a dearth of information about the function of the intracellular domain of many important signal transduction proteins.

The methods disclosed herein advantageously allow for the development of drug screening assays that target the intracellular domain of membrane proteins and/or regulate function of membrane proteins. Because the methods are performed on solubilized integral membrane proteins, the membrane proteins can be screened for selective binding to compounds that are known to exist in cells and/or that are known to have a regulatory function but are not known to bind to the membrane protein. The methods are particularly advantageous because they do not require a crystal structure and are suitable for moderate or high throughput screening. In addition, the present invention relates to methods for screening regulatory binding sites on the intracellular domain of signal transduction proteins using fluorescent regulatory molecules.

II. Methods

In a first embodiment, the present invention relates to a method for identifying molecules that selectively bind to a lipid binding site of a native integral membrane bound protein. The method can include (i) providing a solubilized integral membrane protein in a detergent micelle and having a native folding conformation, wherein the integral membrane protein has a native lipid binding site; (ii) providing a soluble lipid analog that binds to the integral membrane protein at the native lipid binding site and causes a change in fluorescence of a fluorophore when bound as compared to unbound; and (iii) screening the solubilized integral membrane protein for binding to a plurality of compounds, wherein the screening is carried by individually contacting each particular compound with solubilized integral membrane protein in the presence of the soluble lipid analog and detecting whether a change in fluorescence occurs, thereby identifying the compound as an agent that selectively binds the integral membrane protein.

In one embodiment, the soluble lipid analog binds to the membrane protein with specificity at a concentration of at least 100 nM, 250 nM, 500 nM, 1 uM, or 10 uM, and/or less than 100 uM, 10 uM, 1 uM or within a range of any of the foregoing upper and lower endpoints.

The integral membrane protein may be a transduction sensitive receptor. The membrane protein can a cys-loop receptor, a purinergic receptor, a tetrameric cation channel, a g-protein coupled receptor, a tyrosine kinase receptor, a mechano-sensitive channel, a calcium channel, or a TRP channel. The membrane protein may be an ion channel. The integral protein may have a lipid binding site located on the inner leaflet side of the membrane protein.

The membrane protein includes a membrane domain that anchors the native protein into the cell membrane. The membrane domain preferably includes at least one transmembrane helix (i.e., a helix or domain that spans essentially the entire membrane in the native cell). More preferably the membrane protein includes at least 2, 3, 4, 5, 6, 7, or more transmembrane domains or helixes.

The receptor protein can be a neuroreceptor, a hormone receptor, or other cell receptor, or a membrane bound transporter protein. The membrane protein is preferably a signal transducing receptor. The signal transducing receptor can sense a ligand, a voltage, or a mechanical property of the cell. Example membrane proteins that can be used in the methods described herein include cys-loop receptors, purinergic receptors (e.g., p2x receptors), tetrameric cation channels, g-protein coupled receptors, tyrosine kinase receptors, mechano-sensitive channels, calcium channels, TRP channels and the like.

In a preferred embodiment, the membrane protein is ligand gated ion channel. The ligand gated ion channel may be a cys-loop receptor selected from the group consisting of nicotinic acetylcholine, GABAA, GABAA-ρ, glycine and 5-HT3 receptors and combinations thereof.

In another embodiment, the receptor may be a ligand binding transmembrane protein such as G-protein coupled receptor. As described more fully below, GPCRs can be screened for intracellular binding of molecules other than those involved in the GPCR pathway (i.e., intracellular binding of molecules other than G-proteins).

Other proteins that can be screened are transmembrane proteins coupled to a receptor or involved in producing second messengers in a receptor pathway (e.g., adenylyl cyclase).

The membrane protein used in the screening of the present invention is provided solubilized in a detergent and having native folding (i.e., in a detergent micelle). Maintaining folding that is similar or identical to native folding is critical to proper detection of native binding. If the protein folding is substantially disrupted (e.g., solubilized in SDS), the binding will not be representative of native binding conditions in the cell and therefore will not represent selective binding under biological conditions. The membrane proteins may be a multimeric protein and the native folding can include native assembly of the multimeric subunits.

In one embodiment the detergent may include $C_{12}$ maltoside, $C_{10}$ maltoside (n-decyl-b-D-maltoside), n-octyl-b-D-glucoside, octaethylene glycol monododecylether, lauryl dimethylamineN-oxide, or CHAPS.

The integral membrane proteins may be screened using a soluble lipid analog. In one embodiment, the soluble lipid analog is an analog of phosphatidic acid or phosphatidyl inositol phosphate. For example, the analog may be a phosphatidic acid or a phosphatidyl inositol phosphate with a shortened acyl chain so as to give the molecule a desired solubility.

Most native lipids have long fatty acyl side chains rendering them insoluble and difficult to work with in an aqueous environment. For example, phosphatidic acid is insoluble in water. In one embodiment of the invention, phosphatidic acid made soluble by shorting the acyl side chains. For example, phosphatidic acid can be made soluble to 50 mM by shorting the acyl side chains to 8 or less carbons. 8 chain (C8-PA), is suitable for a high throughput probe. The following three structures show a. phosphatidic acid, b. short chain phosphatidic acid, and c. short chain phosphatidic acid with a fluorophore attached.

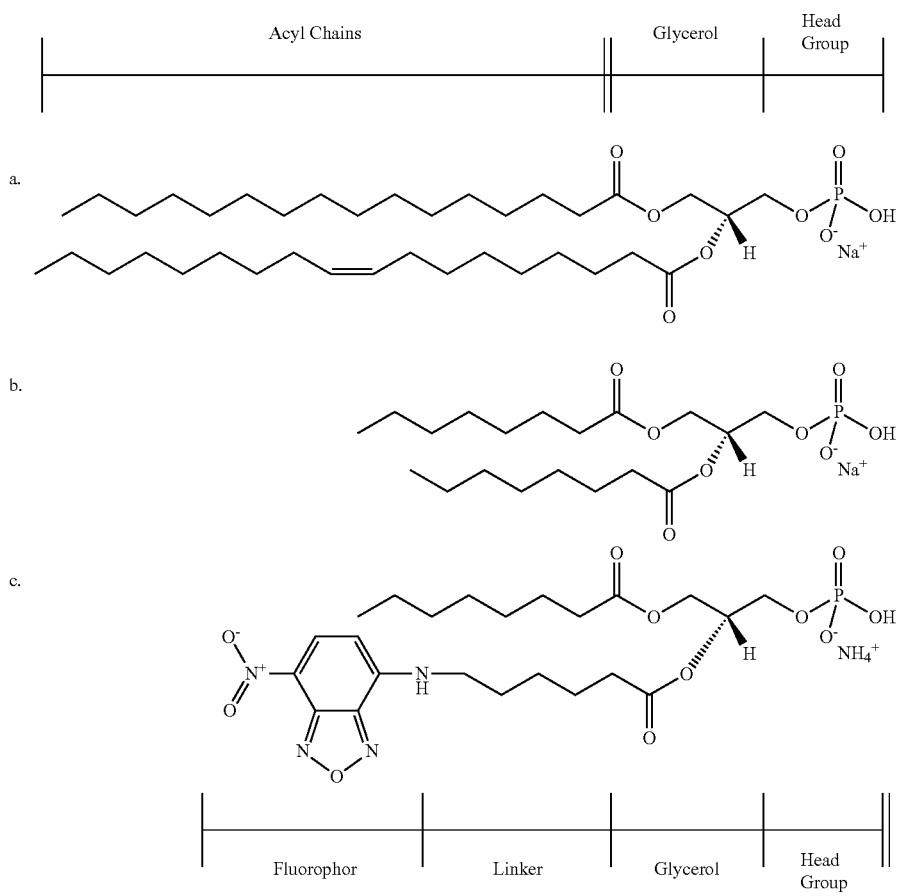

Lipids that can be shortened to produce a soluble lipid analog include sphingolipids, ceramides, sphingosines, sphingosine-1-phosphate, glucosylceramide, ceramide-1-phosphate, phosphatidylinositol phosphates (e.g., PIP2), lysophosphatidic acid, phosphatidic acid, pyrophosphatidic acid, and the like.

The lipid analog changes fluorescence when bound versus unbound. The change in fluorescence is preferably provided by a fluorescent dye or a FRET partner. In one embodiment the dye may be fluorescein or tetramethylrhodamine or other fluorescent dye known in the art and suitable for attaching to an acyl chain or other group of a solubilized lipid analog.

In one embodiment, the lipid analog may include an environmentally sensitive dye. The environmentally sensitive dye changes fluorescence when inserted into the lipid micelle. Examples of polar sensitive dyes include but are not limited to 6-Acryloyl-2-Dimethylaminonaphthalene (Acrylodan) and 6-Bromoacetyl-2-Dimethylaminonaphthalene (Baden), which undergo large changes in Stoke's shifts upon binding to a hydrophobic molecule.

Binding of the fluorophore to the transmembrane domain is expected to shift the emission spectrum and distinguish bound fluorophore from unbound. Baden and Acrylodan will be conjugated to 6,8 chain acyl groups. The linker length and acyl chain will be adjusted to produce the desired solubility.

In one embodiment, the lipid analog (i.e., soluble lipid probe) has 1 or 2 acyl chains and one or both of the acyl chains is less than 10, 9, 8, or 7 carbon and may be saturated, unsaturated, substituted or un-substituted and/or may include a dye (which is not counted for purposes of determining the chain length of the acyl group).

The solubility is important for the probe to be useful in binding to the solubilized membrane protein. In one embodiment, the soluble lipid analog may have a solubility in water of at least 0.1 uM, 0.25 uM, 0.5 uM, 1.0 uM, or 10 uM or less than 100 uM, 10 uM, or 1.0 uM or within a range of any of the foregoing upper and lower endpoints. The soluble lipid analog may have different solubilities than the foregoing when placed in different solvents.

In one embodiment, the protein is provided natively folded in an unpurified or partially purified cell lysate. Cell lysate includes a mixture of (i) the protein of interest, (ii) a detergent that solubilizes the cell membrane, and (iii) substantial quantities of proteins and other cellular molecules not known to be of interest. Providing the protein in cell lysate can be highly advantageous for detecting binding of regulatory molecules. Providing the membrane protein in cell lysate allows the detection of selective binding of a particular molecule where other cellular components might be necessary for the binding. If the membrane protein is purified out of the lysate, the cofactors or additional proteins or molecules necessary for binding to occur to the protein of interest may be removed and the screen will report a negative result. Thus, for purposes of identifying a novel binding site on the intracellular domain, providing the membrane protein in cell lysate can be highly advantageous and in some cases, critical to properly detecting selective binding when screening for compounds not known to bind. However, screening in cell lysate is not required.

The conditions for providing a membrane protein solubilized and having native folding can be obtained using fluorescent size exclusion chromatography (FSEC). The protein of interest is fused with a fluorescent label such as a fluorescent protein (e.g. green fluorescent protein) using techniques known in the art. The fusion protein is expressed in a cell. The cells expressing the membrane protein (i.e., with the fluorescent tag) are lysed using a detergent to produce a cell lysate. The cell lysate is loaded onto a size exclusion column and the proteins are separated according to size. The eluent is analyzed using fluorescence detection. Protein that has a native folding will elute in a peak having a molecular weight that corresponds to the molecular weight of the native protein. Proteins that are not properly folded will form aggregates and elute in the void space. In addition, the peak for the membrane protein can be analyzed to detect how sharp the peak of properly folded molecules may be. Proteins that have a native folding will form a sharp peak. Proteins that are improperly folded and/or unstable will appear in the fraction with the void space and/or a shoulder that broadens out the proper protein peak. To obtain the optimal conditions for providing the protein of interest for the assays of the present invention, the protein of interest can be analyzed under several different lysis conditions and the stability of the protein detected by analyzing the peaks of the fluorescence spectrum.

In one embodiment, the protein is provided in FSEC stabilized extraction conditions. FSEC stabilized extraction conditions are protein sample conditions in which the buffer, pH, detergent type and detergent concentration for solubilizing the membrane protein have been determined by FSEC to yield natively folded protein in detergent.

Additional details regarding method for solubilizing a membrane protein can be found in the journal article by Toshimitsu Kawate and Eric Gouaux, titled "Fluorescence-Detection Size-Exclusion Chromatography for Precrystallization Screening of Integral Membrane Proteins", published in Structure, Volume 14, Issue 4, 673-681, 1 Apr. 2006, the contents of which are hereby incorporated herein by reference.

In another embodiment, the methods of the present invention may include all or a portion of the following steps: (i) selecting a membrane protein having an intracellular domain; (ii) providing the membrane protein as an solubilized integral membrane protein, wherein the extracted protein has a native folding conformation; (iii) screening the membrane protein by independently contacting the intracellular domain of the extracted protein with a plurality of intracellular molecules, wherein the intracellular molecules are not known to bind to the intracellular domain with specificity and identifying whether the intracellular molecules bind with specificity.

In a first step, a native membrane protein is selected. Any native membrane protein can be screened according to the present disclosure so long as the native protein is membrane bound and has at least a portion of the membrane protein that is in contact with the cytosol. For purposes of this invention, the term "intracellular domain" includes the amino acids on the membrane protein that are solvent accessible to the cytosol. Thus, the "intracellular domain" may include portions of a transmembrane helix that extends into the cytosol.

The molecules used to screen the membrane proteins for intracellular ligand binding sites are molecules that are endogenous to the native cells of the native membrane protein. The native cell may or may not be the same cells used to express the membrane protein. The molecules can be nucleic acids, peptides, lipids, carbohydrates, small organic molecules, or combinations of these.

Examples of molecules that can be screened using the methods of the present invention include sphingolipids, ceramides, sphingosines, sphingosine-1-phosphate, glucosylceramide, ceramide-1-phosphate, phosphatidylinositol phosphates (e.g., PIP2), lysophosphatidic acid, phosphatidic acid, pyrophosphatidic acid, platelet activating factor, endocannabinoids, prostaglandins, retinol derivatives, steroids, retinoic acid, prostiglandins, guanyl cyclase, diacyl glycerol compounds, any sugar molecules or derivatives or dimers, trimers, or tetramers of carbohydrates, etc., calcium, or nitric oxide, protein tyrosine phosphatases, tyrosine kinases, and the like.

Other molecules that can be screened are molecules involved in glycolysis, the Krebs cycle, the MAP/ERK pathway, cAMP dependent pathway, IP3/DAP dependent pathway, EnvZ/OmpR osmoregulation system, ATP/histidine residue system, and the like, or any other molecules related to two component regulatory system.

Importantly, the intracellular molecules screened for binding to the membrane proteins include molecules that are not known to bind to the intracellular domain with specificity. In other words, in one embodiment, the method includes screening for novel binding and/or novel binding sites in the native system. This type of screen is critically different than screening known binding sites for compounds that are not endogenous to the native cell. Screening the endogenous molecules leads to binding that modulates the receptors using unknown cellular mechanism. Thus these screens have a high probability of producing molecules that will regulate the membrane proteins and/or molecules associated with the membrane proteins.

In one embodiment, the assay can be carried out using a scintillation proximity assay or fluorescent FRET pairs. To perform the scintillation proximity assay the membrane protein can be attached to a scintillation bead using an antibody. In a preferred embodiment, the antibody is screened for binding to the transmembrane domain or the intracellular domain to ensure that the intracellular domain is bound in close proximity to the scintillation bead. The intracellular molecules are then labeled with a radioactive atom. The radioactive intracellular molecule when bound to the intracellular domain of the membrane protein with specificity will cause the scintillation bead to fluoresce with a greater intensity due to the proximity of the binding.

In an alternative embodiment, the intracellular molecule and the intracellular domain of the membrane protein can both be labeled with a fluorescent molecule that form a fret pair. Binding of the intracellular molecule to the intracellular domain places holds the FRET pair in close proximity and a change in fluorescence can be detected. Additional details regarding methods for using fluorescence to identify binding to a soluble protein using fluorescence is described in U.S. Pat. No. 7,947,466, Issued to Hansen et al. on May 24, 2011, which is hereby incorporated herein by reference.

The assays may be carried out at concentrations of intracellular molecules having a concentration within a factor of 5 fold, 2 fold, or 1.5 fold of the concentrations of the compounds in the native cells. In addition, the temperature, pH, salt concentration, and the like can be carried out under physiological conditions (i.e., non-denaturing conditions).

The assays can also be carried out using inhibitors of various endogenous intracellular enzymes and molecules, including proteases, protease inhibitors, kinases, kinase inhibitors, and the like.

The methods of the present invention are highly advantageous because they can test binding of molecules that are known to be in contact with the intracellular domain of the proteins, but which are not known to bind with specificity. By detecting binding of intracellular molecules, regulatory binding sites on the intracellular domains can be discovered. Since regulatory binding sites are not usually a critical component of the main function of a protein, these regulatory sites can go undetected even though they pose a more benign and/or specific regulation of particular membrane proteins.

Once the novel intracellular binding site has been identified, the soluble membrane proteins can also be used to screen molecules that modulate the membrane proteins at the intracellular binding site. The method includes using a screening ligand that selectively binds to the intracellular domain and produces a change in fluorescence when bound. For example, the screening ligand may be an intracellular molecule identified using the method described above as selectively binding to the intracellular domain. The intracellular agent or a derivative or analog of the intracellular molecule can be used in an assay to screen compounds such as non-endogenous (i.e., non-native) compounds for modulation of the membrane proteins. In one embodiment, the assay can be a competitive assay. Molecules competitive to the binding site of the intracellular compound will disrupt binding of the intracellular molecule and cause a change in fluorescence, thereby indicating selective binding.

The methods performed using the identified intracellular compound or a derivative or analog thereof as a screening ligand can be performed on a recombinant solubilized integral membrane protein. The assay may be carried out in lysate or a purified protein and/or a purified protein with any necessary cofactors included. When screening for non-endogenous molecules, it can be helpful to purify the protein because the known binding of the endogenous intracellular molecules (using the methods described above) reduces the complexity of knowing what molecules are necessary for ligand binding. Thus, the assay can be carried out in a more pure system with greater assurances that the necessary components are present.

However, whether the protein is purified or in lysate, the protein must have sufficiently native folding so as to ensure similar binding to the native protein. In one embodiment, the screening assay on non-native molecules is carried out on the intracellular domain using an FSEC stabilized extraction medium. As described above. The fluorescent screening can be carried out using compounds and methods described in U.S. Pat. No. 7,947,466, incorporated herein by reference. For example, the assay can include using drug libraries and high throughput techniques to identify molecules that bind to the membrane proteins. However, in contrast to the methods in '466 patent the detection in the present invention is related to detecting binding to the intracellular domain and the ligand that changes fluorescence when bound is identified using the methods described herein. The non-native compounds identified using the methods of the invention can also be screened against the membrane proteins in cells or tissues (i.e., membrane bound) or can be modified to make new libraries of non-native compounds that can also be screened using the methods described herein and/or screened against the membrane proteins in cells or tissue (i.e, membrane bound).

In one embodiment, the ligand that changes fluorescence when bound versus not bound is a radioactive phosphatidic acid molecule that binds to the intracellular domain of a nicotinic receptor and the nicotinic receptor is bound to a scintillation bead. The phosphatidic acid may have a radio labeled phosphorous or a radio labeled carbon or other atom. The assay may be carried out by screening compounds that disrupt fluorescence from the scintillation beads using a SPA assay. The phosphatidic acid molecule may be phosphatidic acid or a derivative thereof (e.g., a more soluble form of phosphatidic acid that has two or more carbons removed from an acyl chain). The phosphatidic acid may alternatively have a GFP attached that FRETs with a GFP attached to the intracellular domain of the nicotinic receptor.

III. Methods for Identifying Lipid Specificity in Nuclear Receptors

Nuclear Receptors (NR) are a class of proteins in cells that respond to steroids and other lipophilic hormones. NR's act by directly binding to DNA and modulating gene expression thereby modulating cell homeostasis. A class of NR's binds to phospholipids for example steroidogenic factor 1 (SF-1). Cardiolipin phospholipid with two glycerol backbones and four acyl chains. The molecule is effectively to phospholipids linked through a phosphate head group. This linkage allows one set of acyl chains to be inserted into a lipid membrane and the second set of acyl chains to be available for binding to a lipid binding site. NRs bound to a cardiolipin or cardiolipin like lipid are localized to a membrane through the lipid linkage.

The present disclosure describes a method for screening for nuclear receptors with lipid binding sites. In a first method a lipid is immobilized to a solid support such as a sephadex bead. The lipid can be synthesized with a biotin, amide, or other suitable functional group for linkage to a solid support (these linkage techniques are well known in the art). In the case of cardiolipin one of the acyl chains can be shortened for solubility and paired with a lipid capable of linking to a solid support. Nuclear receptor proteins can then be passed across immobilized cardiolipin (or cardiolipin like lipids) and assayed for specific binding of a cardiolipin. In one case the immobilized lipid is a homogeneous lipid. In a second case cardiolipin with varying acyl side chains can be synthesized and immobilized. The bound NR can be released by hydrolyzing the phospholipid with a lipase capable of hydrolyzing cardiolipin (known in the art). The released protein can then be assayed to identify the NR and or to identify. In the case were a mixture of acyl chains was immobilized, the cleaved lipid bound to the NR can also be assayed to identify a preferential lipid binding to a NR. Mass spectrometry is a suitable assay for identifying proteins and lipids released after treatment with a lipase.

Alternative assays can be performed where a lipid is linked to a solid support and then cleaved from the solid support with a enzymatic reaction. For example a lipid could be linked with a peptide and then the peptide can be cleaved with a protease, or a lipid can be linked with a disulfide and then released by reducing the disulfide bond.

Soluble lipid analogs that bind to nuclear receptors can be screened using fluorescent assays as described above except that the lipid binding site is present in a nuclear receptor. In a second assay, binding of nuclear receptor to immobilized lipid can be blocked by compounds that are selective for nuclear receptors.

Any of the foregoing embodiments described above may be used alone or in combination with one another and/or the embodiments disclosed in the references incorporated herein by reference.

The illustrative embodiments described in the detailed description and claims are not meant to be limiting. Other embodiments may be utilized, and other changes may be made, without departing from the spirit or scope of the subject matter presented herein. It will be readily understood that the aspects of the present disclosure, as generally described herein can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed:

1. A method for identifying molecules that selectively bind to a lipid binding site of a native integral membrane bound protein, comprising:
   (i) providing a solubilized integral membrane protein in a detergent and having a native folding conformation, wherein the integral membrane protein is an ion channel having a native lipid binding site;
   (ii) providing a soluble lipid mimetic probe that binds to the integral membrane protein at the native lipid binding site and causes a change in fluorescence of a fluorophore when bound as compared to unbound;
   (iii) screening the solubilized integral membrane protein for binding to a plurality of compounds, wherein the screening is carried by individually contacting each particular compound with solubilized integral membrane protein in the presence of the soluble lipid mimetic probe and detecting whether a change in fluorescence occurs, thereby identifying the compound as an agent that selectively binds the integral membrane protein.

2. The method of claim 1, wherein the soluble lipid mimetic probe binds to the membrane protein with specificity at a concentration of at least 500 nM.

3. The method of claim 1, wherein the membrane protein is a transduction sensitive receptor.

4. The method of claim 1, wherein the ion channel is a cys-loop receptor, purinergic receptor, tetrameric cation channel mechano-sensitive channel, a calcium channel, or a transient receptor potential ("TRP") channel.

5. The method of claim 1, wherein the membrane protein has a ligand binding domain that is distinct from the lipid binding site.

6. The method of claim 1, wherein the lipid binding site is located on the inner leaflet side of the membrane protein.

7. The method of claim 1, wherein the soluble ligand analog is an analog of phosphatidic acid or phosphatidylinositol phosphate.

8. The method of claim 1, wherein the membrane protein is solubilized in a detergent comprising n-octyl-β-D-glucoside, octaethylene glycol monododecylether, lauryl dimethylamine-N-oxide, or 3-[(3-cholamidopropyl)dimethylammonio]-1-propanesulfonate ("CHAPS").

9. The method of claim 1, wherein the membrane protein is solubilized in a detergent comprising $C_{12}$ maltoside or $C_{10}$ maltoside.

10. The method of claim 1, wherein the membrane protein is solubilized in a detergent micelle.

11. The method of claim 1, wherein the lipid analog has two acyl chains.

12. A method as in claim 1, wherein the soluble lipid mimetic probe comprises:
    (i) a head group and a portion of one or more acyl chains, the lipid mimetic probe having a structure that binds the lipid binding site;
    (ii) a fluorophore; and
    wherein the soluble lipid mimetic probe has a solubility in water of at least 0.20 μM.

13. The as in claim 12, wherein the solubility of the probe is at least 1 μM.

14. The as in claim 12, wherein the fluorophore is environmentally sensitive.

15. The method as in claim 12, wherein the fluorophore is sensitive to hydrophobicity.

16. The soluble lipid mimetic probe as in claim 12, wherein the fluorophore comprises fluorescein or rhodamine.

17. The probe of claim 12, wherein the lipid mimetic method is an analog of phosphatidic acid or phosphatidylinositol phosphate.

18. The probe of claim 12, wherein the lipid mimetic method has two acyl chains, wherein one or both are a shortened acyl chain with a chain length of 10 or fewer carbons.

19. The probe of claim 18, wherein one of the two acyl chains is polyunsaturated.

* * * * *